United States Patent
Zhang et al.

(10) Patent No.: US 9,789,049 B2
(45) Date of Patent: *Oct. 17, 2017

(54) WATER RESISTANT PERSONAL CARE POLYMERS

(71) Applicants: Dow Global Technologies LLC, Midland, MI (US); Rohm and Haas Company, Philadelphia, PA (US)

(72) Inventors: Li Zhang, Ambler, PA (US); Fanwen Zeng, Belle Mead, NJ (US)

(73) Assignees: Rohm and Haas Company, Philadelphia, PA (US); Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/231,052

(22) Filed: Aug. 8, 2016

(65) Prior Publication Data

US 2016/0338940 A1    Nov. 24, 2016

Related U.S. Application Data

(63) Continuation of application No. 14/366,193, filed as application No. PCT/US2012/068898 on Dec. 11, 2012, now Pat. No. 9,486,399.

(60) Provisional application No. 61/579,033, filed on Dec. 22, 2011.

(51) Int. Cl.

| | |
|---|---|
| *A61K 8/81* | (2006.01) |
| *A61Q 17/04* | (2006.01) |
| *C08F 220/14* | (2006.01) |
| *C08F 220/18* | (2006.01) |
| *A61K 8/35* | (2006.01) |
| *A61K 8/37* | (2006.01) |
| *C08F 220/68* | (2006.01) |
| *C08F 220/06* | (2006.01) |
| *C08F 220/40* | (2006.01) |

(52) U.S. Cl.
CPC .............. *A61K 8/8152* (2013.01); *A61K 8/35* (2013.01); *A61K 8/37* (2013.01); *A61Q 17/04* (2013.01); *C08F 220/14* (2013.01); *C08F 220/18* (2013.01); *C08F 220/68* (2013.01); *A61K 2800/48* (2013.01); *A61K 2800/594* (2013.01); *C08F 220/06* (2013.01); *C08F 220/40* (2013.01); *C08F 2220/1833* (2013.01)

(58) Field of Classification Search
None
See application file for complete search history.

(56) References Cited

U.S. PATENT DOCUMENTS

| | | | |
|---|---|---|---|
| 4,552,755 | A | 11/1985 | Randen |
| 4,762,703 | A | 8/1988 | Abrutyn |
| 6,471,952 | B1 | 10/2002 | Dubief et al. |
| 7,416,739 | B2 | 8/2008 | Baxter et al. |
| 7,629,414 | B2 | 12/2009 | Bardman et al. |
| 2003/0021847 | A1 | 1/2003 | Baxter et al. |
| 2004/0109834 | A1 | 6/2004 | Tamazawa |
| 2005/0220729 | A1 | 10/2005 | Luukas et al. |
| 2010/0104610 | A1 | 4/2010 | Dueva-Koganov et al. |
| 2010/0129303 | A1 | 5/2010 | Dueva-Koganov et al. |

FOREIGN PATENT DOCUMENTS

| | | |
|---|---|---|
| EP | 1209213 A1 | 5/2002 |
| EP | 1273286 A2 | 1/2003 |
| EP | 1486514 A1 | 12/2004 |
| EP | 1273635 B1 | 11/2007 |
| JP | H03-206023 A | 9/1991 |
| JP | 2003226793 | 8/2003 |
| WO | 2010/043588 A1 | 4/2010 |
| WO | 2010/046197 A2 | 4/2010 |

*Primary Examiner* — Jennifer A Berrios
(74) *Attorney, Agent, or Firm* — Edward L. Brant

(57) ABSTRACT

Described are personal care compositions comprising a polymer comprising: (a) one or more polymer comprising, as polymerized units, (i) 75% to 35% by weight, based on the weight of said polymer, one or more (meth)acrylate monomer selected from at least one of C1-C4 (meth)acrylate, (meth)acrylic acid, styrene, or substituted styrene, and (ii) 25% to 65% by weight, based on the weight of said polymer, one or more hydrophobic monomer, including hydrophobically substituted (meth)acrylate monomers, with alkyl chain length from C8 to C22 and, (iii) optionally crosslinker, and, (b) at least one suncare active. Optionally, the polymer further includes a stage 2 polymer comprising, as polymerized units, (i) 10-99% of one or more monomer which has a Tg of more than 80° C. after polymer formation, (ii) 1-10% of one or more (meth)acrylate monomer containing acid functional group, and (iii) optionally, a crosslinker.

6 Claims, No Drawings

WATER RESISTANT PERSONAL CARE POLYMERS

CROSS-REFERENCE TO RELATED APPLICATIONS

This application is a continuation of U.S. application Ser. No. 14/366,293 filed on Jun. 17, 2014, which is a 371 U.S.C. §371 national phase application of International Application No. PCT/US12/068898, filed on Dec. 11, 2012, which claims priority from U.S. Provisional Application Ser. No. 61/579,033, filed Dec. 22, 2011, all of which are incorporated herein by reference in their entireties.

FIELD

The present invention relates to compositions for imparting water resistance and aiding retention of active ingredients in personal care compositions.

BACKGROUND

The need for compositions for imparting water resistance and aiding retention of active ingredients in personal care compositions is well known. Without them, personal care actives, such as sun care actives, may wash off, wear off, be re-emulsified, or otherwise lose their efficacy. The problem with current water resistance imparting polymers is they are typically very tacky and impart bad aesthetic feel to consumers when formulated in sunscreen formulations. For reference, aesthetics is one of the most important considerations in a consumer's selection of, or at least loyalty to, a personal care composition.

Accordingly, what is needed is a water resistance polymer which possesses improved aesthetic performance, as well as excellent retention of active ingredients when water is present.

DETAILED DESCRIPTION

In one embodiment, the present invention provides personal care compositions comprising a polymer comprising: (a) one or more polymer comprising, as polymerized units, (i) 75% to 35% by weight, based on the weight of said polymer, one or more (meth)acrylate monomer selected from at least one of C1-C4 (meth)acrylate, (meth)acrylic acid, styrene, or substituted styrene, and (ii) 25% to 65% by weight, based on the weight of said polymer, one or more hydrophobic monomer, including hydrophobically substituted (meth)acrylate monomers, with alkyl chain length from C8 to C22 and, (iii) optionally crosslinker, and, (b) at least one suncare active. The resulting polymer shows superior aesthetic feel, great film formation, and has excellent retention of active ingredients in the presence of water.

As used herein, "(meth)acrylic" means acrylic or methacrylic; "(meth)acrylate" means acrylate or methacrylate; and "(meth)acrylamide" means acrylamide or methacrylamide. "Substituted" means having at least one attached chemical group such as, for example, alkyl group, alkenyl group, vinyl group, hydroxyl group, carboxylic acid group, other functional groups, and combinations thereof.

Styrene and substituted Styrene monomers have one ethylenically unsaturated group per molecule. Examples of Styrene and substituted Styrene monomers include 4-methylstyrene, 2-methylstyrene, 3-methylstyrene, 4-methoxystyrene, 2-hydroxymethylstyrene, 4-ethylstyrene, 4-ethoxystyrene, 3,4-dimethylstyrene, 2-chlorostyrene, 3-chlorostyrene, 4-chloro-3-methylstyrene, 4-t-butylstyrene, 2,4-dichlorostyrene, 2,6-dichlorostyrene. Preferred Styrene and substituted Styrene monomers include styrene (Sty) and 4-methylstyrene (vinyltoluene).

Preferred (meth)acrylate monomer containing acid functional group include acrylic acid, methacrylic acid, itaconic acid, crotonic acid. More preferred (meth)acrylate monomers containing acid functional group are acrylic acid, methacrylic acid.

In one embodiment, monomer (i) is present in a range of 75% to 35% by weight. Preferred monomer (i) are (meth)acrylate monomer with alkyl chain length of C4 and less, styrene, substituted styrene, More preferred monomer (i) are butyl acrylate, ethyl acrylate, acrylic acid, methyl methacrylate, ethyl methacrylate, butyl methacrylate, methacrylic acid, styrene. Most preferred monomer (i) are butyl acrylate, methyl methacrylate, methacrylic acid, styrene. In one embodiment, wherein monomer (ii) is one or more hydrophobic monomer, including hydrophobically substituted (meth)acrylate monomers, with alkyl chain length from C8 to C22. Preferred monomers (ii) are one or two monomer selected from ethylhexyl methacrylate, lauryl methacrylate, stearyl methacrylate, and cetyl-eicosyl methacrylate, behenyl methacrylate, ethylhexyl acrylate, lauryl acrylate, stearyl acrylate, and cetyl-eicosyl acrylate, behenyl acrylate. Most preferred monomer (ii) are one or two monomer selected from ethylhexyl acrylate, lauryl methacrylate, stearyl methacrylate.

In some embodiments, the polymer further comprising a cross-linker Crosslinkers are monomers having two or more ethylenically unsaturated groups, and may include, e.g., divinylaromatic compounds, di-, tri- and tetra-(meth)acrylate esters, di-, tri- and tetra-allyl ether or ester compounds and allyl (meth)acrylate. Preferred examples of such monomers include divinylbenzene (DVB), trimethylolpropane diallyl ether, tetraallyl pentaerythritol, triallyl pentaerythritol, diallyl pentaerythritol, diallyl phthalate, diallyl maleate, triallyl cyanurate, Bisphenol A diallyl ether, allyl sucroses, methylene bisacrylamide, trimethylolpropane triacrylate, allyl methacrylate (ALMA), ethylene glycol dimethacrylate (EGDMA), hexane-1,6-diol diacrylate (HDDA) and butylene glycol dimethacrylate (BGDMA). Especially preferred crosslinkers include DVB, ALMA, EGDMA, HDDA and BGDMA. Most preferred crosslinker is ALMA. In some embodiments of the invention, the amount of polymerized crosslinker residue in the polymer is at least 0.01%, alternatively at least 0.02%, alternatively at least 0.05%. In some embodiments of the invention, the amount of crosslinker residue in the polymer is no more than 0.3%, alternatively no more than 0.2%, alternatively no more than 0.15%. Polymers usefully employed according to the invention can be prepared by conventional emulsion, solution or suspension polymerization. Emulsion polymerization is preferred. Monomers used to prepare the polymers are added in a sequential process or randomly to afford non-random or random polymers using a free-radical initiator such as peroxygen compounds or diazo compounds and, optionally, chain transfer agents. The length of the primary polymer chains is typically such that, if any crosslinks were removed, the molecular weight (Mw) would be in the range of about 50,000 to 10,000,000, alternatively from 100,000 to 5,000,000, alternatively from 200,000 to 2,000,000.

A free radical initiator is utilized in solution and emulsion polymerizations. Suitable free radical initiators include hydrogen peroxide; tert-butyl hydroperoxide; sodium, potassium, lithium and ammonium persulfate and the like. A reducing agent, such as a bisulfate, including an alkali metal metabisulfite, hydrosulfite, and hyposulfite; and sodium formaldehyde sulfoxylate or a reducing sugar such as ascorbic acid or isoascorbic acid, may be used in combination with the initiator to form a redox system. Initiators usefully employed for suspension polymerization include oil soluble peroxides, hydroperoxides and azo compounds such as AIBN. The amount of initiator may be from 0.01% by weight to about 2% by weight of the monomer charged and in a redox system, a corresponding range of 0.01% by weight to about 2% by weight of reducing agent may be used. Transition metal catalysts, such as iron and copper salts, may be used.

The polymerization temperature may be in the range of about 10° C. to 120° C. in the aqueous emulsion, suspension and solution polymerizations. In the case of the persulfate systems, the temperature is preferably in the range of 60° C. to 90° C. In the redox system, the temperature is preferably in the range of 20° C. to 70° C.

For emulsion polymers, any emulsifiers or dispersing agents optionally employed for preparing the monomer emulsions or polymer emulsions may be anionic, cationic or non-ionic types. Also a mixture of any two or more types may be used. Suitable nonionic emulsifiers include, but are not limited to, ethoxylated octylphenols, ethoxylated nonylphenols, ethoxylated fatty alcohols and the like. Suitable anionic emulsifiers include, but are not limited to, sodium lauryl sulfate, sodium dodecylbenzene sulfonate, sulfated and ethoxylated derivatives of nonylphenols, octylphenols and fatty alcohols, esterified sulfosuccinates and the like. Suitable cationic emulsifiers include, but are not limited to, laurylpyridinium chlorides, cetyldimethylamine acetate, ($C_8$-$C_{18}$) alkyldimethylbenzylammonium chlorides and the like. The level of emulsifier may be from about 0.1% to about 10% by weight, based on total monomer charged.

In one embodiment, monomer (i) is at least two of butyl acrylate, methyl methacrylate, methacrylic acid, or styrene.

In one embodiment, monomer (ii) is at least one of ethylhexyl acrylate, lauryl methacrylate, stearyl methacrylate, and cetyl-eicosyl methacrylate, behenyl methacrylate, lauryl acrylate, stearyl acrylate, and cetyl-eicosyl acrylate, behenyl acrylate. In one embodiment, monomer (ii) is at least two of ethylhexyl acrylate, lauryl methacrylate, stearyl methacrylate, and cetyl-eicosyl methacrylate, behenyl methacrylate, lauryl acrylate, stearyl acrylate, and cetyl-eicosyl acrylate, behenyl acrylate.

In one embodiment, the polymer is formed in a single stage.

In one embodiment, the polymer is formed in a two stage reaction. In one embodiment, the stage 2 polymer comprises, as polymerized units, (i) 10-99% of one or more monomer which has a Tg of more than 80° C. after polymer formation, (ii) 1-10% of one or more (meth)acrylate monomer containing acid functional group, and (iii) optionally, a crosslinker. In one embodiment, the stage 1 and stage 2 ratio ranges from 60:40 to 99 to 1.

Polymers with high glass transition temperatures ("Tg") are typically used to lower the tackiness of polymer film properties. However, high Tg polymers have the drawback that they form films that are extremely hard and brittle. Preferably, the Tg of the second stage polymer is in the range of about 50 to 200° C., alternatively from 75 to 150° C., alternatively from 80 to 120° C.

In some embodiments of the invention, the stage 1 and stage 2 ratio is more than 50:50, preferably more than 60:40. In some embodiments of the invention, the stage 1 and stage 2 ratio is less than 99:1, preferably, less than 90 to 10.

The invention provides water resistance polymers, personal care compositions and formulations including any cosmetically acceptable oil base. A suitable oil base includes any oil or mixture of oils which are conventionally used in the personal care products. Examples include saturated fatty esters and diesters, such as isopropyl palmitate, octyl palmitate, butyl stearate, isocetyl stearate, octadodecyl stearoyl stearate, diisopropyl adipate, dioctyl sebacate, paraffin oils, paraffin waxes, animal oils and vegetable oils such as mink oil, coconut oil, soybean oil, palm oil, corn oil, cocoa butter, sesame oil, lanolin oil, fatty alcohols such as stearyl alcohol, isostearyl alcohol, isocetyl alcohol. The oils listed are merely examples are not intended to limit the invention in any way. In general, any hydrophobic material or mixtures thereof which are toxicologically safe for human or animal use may constitute the oil base of the present invention.

The personal care compositions and formulations containing the water resistance polymers are of four basic compositions: oil dispersions, oil-in-water emulsions, water-in-oil emulsions and solutions from one or more organic solvents. The oil dispersions are prepared by dispersing the water resistance polymers in the oil base with one or more active ingredients. The water resistance polymers can be dispersed in an oil phase or are prepared as an aqueous suspension prior to preparing the final oil-in-water or water-in-oil emulsion. The polymers can be added in either phase at any stage in preparing the composition or formulation. Personal care formulations are prepared by combining water resistance polymers, an oil base, optionally including an aqueous phase, one or more active ingredients and optional additives by warming the mixture with slow agitation. The oil based personal care compositions and formulations include from 0.01 to 10% by weight of at least one water resistance polymer based on the total weight of the formulation. The cosmetically acceptable base of the compositions and formulations may be solid or liquid, but the entire formulation is preferably fluid at skin temperatures for ease of application. Suitable solvents for preparing a solution of the polymer are typically those used in the art and include alcohols such as ethyl alcohol and volatile silicones such as cyclomethicone. Suitable additives include fragrances, fillers, dyes, colorants, preservatives, biocides, antioxidants, other such additives conventionally used in personal care products without negatively impacting substantivity and combinations thereof. The invention provides dermally applied personal care compositions and formulations including water resistance polymers dispersed in an oil base and one or more active ingredients. Suitable active ingredients include but are not limited to sunscreening actives, moisturising actives such as moisturizing oils, cleansing actives for personal care, detergent actives for personal care, vitamins, folic acid derivatives, exfoliating agents, deodorising actives, fragrance actives, skin exfoliating actives, topical medicament actives for personal care, cosmetic agents for personal care, hair conditioners, facial care products, body washes, topical preparations, infrared (IR)-absorbing materials for personal care, acne medications and combinations thereof. Cosmetic agents include for example mascaras, eyeliners, lipsticks, powders, paints, foundations and masks.

Suitable sunscreen actives include inorganic oxides such as titanium dioxide and zinc oxide, cinoxate(2-ethoxyethyl-p-methoxy-cinnamate); diethanolamine-p-methoxycinnamate; digalloyl trioleate ethyl 4-bis(hydroxypropyl)aminobenzoate; ethylhexyl-p-methoxy-cinnamate; 2-ethylhexyl salicylate; glyceryl aminobenzoate; homosalate(3,3,5-trimethylcyclohexyl salicylate); triethanolamine salicylate; 2-phenyl-benzimidazole-5-sulfonic acid; sulisobenzone(2- hydroxy-4-methoxy-benzophenone-5-sulfonic acid); Padimate A (amyl p-dimethylaminobenzoate); Padimate O (octyl dimethyl para aminobenzoate); Octocrylene, Avobenzone, Ecamsule, 4-Methylbenzylidene camphor, Tinosorb M (BASF), Tinosorb S (BASF), Neo Heliopan AP, Mexoryl XL, Benzophenone-9, Uvinul T 150 (BASF), Uvinul A Plus (BASF), Uvasorb HEB (3V Sigma), Parsol SLX (DSM Nutritionals), sopentenyl-4-methoxycinnamate, and menthyl anthranilate, Sun-Spheres® (The Dow Chemical Company) and mixtures thereof.

The sunscreen compositions and formulations also may include a sunscreen material particularly suitable for ultraviolet-A (320-400 nm) protection. This compound suitably is selected from oxybenzone, dioxybenzone; 2-ethylhexyl-2-cyano-3,3 diphenylacrylate; methyl benzilidine camphor; 4-t-butyl-4'-methoxydibenzoyl-methane and mixtures thereof.

Sunscreen compositions and formulations of the invention may be formed using conventional emulsion techniques and inexpensive agitation equipment. The sunscreen compositions and formulations thus formed are stable emulsions, the polymers effectively retaining active ingredients at low polymer concentrations, ranging from 0.01 to 10% by polymer weight based on the total weight of the composition in the oil phase; the formulation having an oil phase viscosity of at least 10 poise under a shear stress up to 1000 dynes/$cm^2$. It is preferred that the formulation consists of an oil-in-water emulsion.

When applied to mammalian skin, these personal care compositions and formulations of the present invention form an oil film on the skin surface. This film gives the skin a moist, glossy appearance which provides cosmetic elegance.

The films helps protect the skin from the drying, oxidizing effects of the environment, and the ultraviolet light-absorber protects the skin from the damaging rays of the sun. The polymer retains the ultraviolet light-absorber onto the skin so that a significantly greater percentage of sunscreen protection is provided at lower polymer concentrations after than with compositions not containing one or more active retaining polymers. Moreover the compositions and formulations remain substantive for extended periods of time and prolonged exposure to aqueous environments such as water, humidity or perspiration.

Oil-in-water emulsions are generally prepared by heating the oil and water phases, and slowly adding the water phase to the oil phase with good agitation. Homogenization may be helpful, but it is not necessary. The addition of low levels of stabilizing ingredients in the water phase has been shown to be helpful. Salts such as magnesium sulfate have proven to be useful emulsion stabilizers, and they do not significantly affect the water resistance of the formulations. The addition of water soluble gums such as guar derivatives, xanthan gum, and aloe vera and thickeners such as hydroxyethyl cellulose, hydroxymethyl cellulose and carboxyvinyl polymers have been found to be helpful in stabilizing the emulsions.

The personal care compositions and formulations are usefully employed in accordance with the present invention as creams, lotions, gels, towelettes, wipes, masks, adhesive pads, sprays delivered from solvent and any conventional means used in personal care art.

The following examples illustrate specific aspects and particular embodiments of the invention which, however, are not to be construed as limited thereby.

EXAMPLES

The following abbreviations are used in the Examples described herein:

BA=butyl acrylate

Sty=Styrene

MAA=methacrylic acid

MMA=methyl methacrylate

EHA=ethylhexyl acrylate

SMA=Stearyl methacrylate

CEMA=Cetyl-eicosyl methacrylate

ALMA=allyl methacrylate

Example 1

One stage polymers of the present invention are listed in TABLE 1:

TABLE 1

| | Composition |
|---|---|
| Polymer 1 | 31 SMA/25 BA/29 Sty/15MAA |
| Polymer 2 | 20 BA/40EHA/38.5 MMA/1.5 MAA/0.075 ALMA |

A standard emulsion polymerization method is used. For example, to a 2-liter round-bottom flask equipped with a overhead stirrer, thermocouple, condenser and inlets for the addition of monomer and initiators is charged 183.5 g of deionized water, 26.6 g of 50% CAVASOL™ W7 M TL (cyclodextrin from Wacker Fine Chemicals), 6.1 g of a 30% DISPONIL® FES 32 (Cognis) surfactant and 1.8 g of sodium carbonate. The flask is stirred and heated to 92° C. A monomer emulsion is prepared by charging 363 g of deionized water and 13.6 g of DISPONIL® FES 32 surfactant to an appropriate container and set to stir. After the surfactant is incorporated into the water, 175 g of BA, 203 g of Styrene, 105 g of MAA and 217 g of SMA is added slowly to the stirring mixture. A cofeed catalyst solution is also prepared by charging 0.69 g of sodium persulfate and 96 g of deionized water.

At reaction temperature of 92° C., 25 g of the above prepared monomer emulsion is charged to the kettle with a 11 gram deionized water rinse, followed by an initiator solution of 2.11 g sodium persulfate and 12 g water.

After initial polymerization and at 85° C., the monomer emulsion cofeed is begun at a rate of 6.33 g per minute for 10 minutes and 12.7 g per minute for 75 minutes. Simultaneously, the catalyst cofeed is begun at a rate of 1.1 g per minute for 88 minutes. At the completion of the monomer emulsion and catalyst cofeed, the reaction mixture is chased to reduce the amount of residual monomers. The resulting Polymer 1 latex has the following characteristics. Solids is the weight of solid material left when the latex is evaporated to dryness, as a percentage of the total weight of latex. Grit is the amount of material retained in the mesh bags. Mean particle size was measured with a Brookhaven Instruments Corp. BI-90 device. Residual Monomer amounts were measured by head space gas chromatography.

Solids: 44.7%

Grit: <100 ppm

Mean Particle Size: 205 nm

Residual Styrene: 7 ppm

Polymer 2 is made substantially as described above, the appropriate changes being made.

Example 2 (Comparative)

Comparative one stage polymers are listed in TABLE 2:

TABLE 2

| | Composition |
|---|---|
| Comparative example A | 31 CEMA/49 BA/18.6 MMA/1.4 MAA |

The comparative polymer is made substantially as described in Example 1, the appropriate changes being made.

Example 3

Two stage polymers of the present invention are listed in TABLE 3:

TABLE 3

| | Composition |
|---|---|
| Polymer 3 | Stage 1 (85%): 31 SMA/25 BA/29 STY/15 MAA<br>Stage 2 (15%): 99 MMA/1 MAA |
| Polymer 4 | Stage 1 (80%): 31 SMA/25 BA/29 STY/15 MAA<br>Stage 2 (20%): 99 MMA/1 MAA |
| Polymer 5 | Stage 1 (70%): 31 SMA/25 BA/29 STY/15 MAA<br>Stage 2 (30%): 99 MMA/1 MAA |
| Polymer 6 | Stage 1 (85%): 20 BA/40 EHA/38.5 MMA/1.5 MAA//0.075 ALMA<br>Stage 2 (15%): 99 MMA/1 MAA |
| Polymer 7 | Stage 1 (80%): 20 BA/40 EHA/38.5 MMA/1.5 MAA//0.075 ALMA<br>Stage 2 (20%): 99 MMA/1 MAA |
| Polymer 8 | Stage 1 (70%): 20 BA/40 EHA/38.5 MMA/1.5 MAA//0.075 ALMA<br>Stage 2 (30%): 99 MMA/1 MAA |
| Polymer 9 | Stage 1 (80%): 20 BA/40 EHA/38.5 MMA/1.5 MAA//0.075 ALMA<br>Stage 2 (20%): 99 MMA/1 MAA//0.075 ALMA |

A standard emulsion polymerization method is used. For example, for Polymer 9, 252 g of deionized water, 8 g of a 23% sodium dodecyl benzene sulfonate and 2 g of sodium carbonate are charged to a 2-liter round-bottom flask equipped with a overhead stirrer, thermocouple, condenser and inlets for the addition of monomer and initiators. The flask is stirred and heated to 92° C. A monomer emulsion (stage 1) is prepared by charging 146 g of deionized water and 5.6 g of sodium dodecyl benzene sulfonate (23%) to an appropriate container and set to stir. After the surfactant is incorporated into the water, 90 g of BA, 180 g of g of EHA, 174 g of MMA, 6.8 g of MAA, and 0.34 g of ALMA is added slowly to the stirring mixture. A cofeed catalyst solution is also prepared by charging 0.86 g of sodium persulfate and 50 g of deionized water.

At reaction temperature of 88° C., 19 g of the above prepared monomer emulsion is charged to the kettle with 5 g of deionized water rinse, followed by an initiator solution of 1.9 g sodium persulfate and 15 g water. After initial polymerization and at 85° C., the stage 1 monomer emulsion cofeed is begun at a rate of 4.72 g per minute for 15 minutes and 10.1 g per minute for 83 minutes. Simultaneously the stage 1 catalyst cofeed is begun at a rate of 0.61 g per minute for 88 minutes. At the completion of the monomer emulsion and catalyst cofeed, the reaction mixture is held for 10 minutes.

During the feed of stage 1, stage 2 monomer emulsion and catalyst are prepared. Stage 2 monomer emulsion is prepared by charging 52 g of deionized water and 2 g of sodium dodecyl benzene sulfonate (23%) to an appropriate container and set to stir. After the surfactant is incorporated into the water, 112 g of MMA, 1.1 g of g of MAA, and 0.09 g of ALMA is added slowly to the stirring mixture. A stage 2 cofeed catalyst solution is also prepared by charging 0.12 g of sodium persulfate and 14 g of deionized water. Upon the completion of stage 1 hold, the stage 2 monomer emulsion cofeed is begun at a rate of 6.55 g per minute for 29 minutes. At the completion of the stage 2 monomer emulsion and catalyst cofeed, the reaction mixture is chased to reduce the amount of residual monomers. The resulting latex has the following characteristics.

Solids: 43.5%
Grit: <100 ppm
Mean Particle Size: 103 nm
Residual EHA: 29 ppm

Polymers 3-8 are made substantially as described above, the appropriate changes being made.

Example 4

To test for aesthetic testing and water-resistance evaluation, a sunscreen base (1) and a nonionic sunscreen base (2) are prepared with the components listed in TABLE 4 in weight percent.

TABLE 4

| Phase | Component | Sunscreen 1 | Sunscreen 2 |
|---|---|---|---|
| A | Deionized Water | qs. to 100 | qs. to 100 |
| | Disodium EDTA | 0.10 | — |
| | Carbomer | 0.2 | 0.2 |
| | Propylene Glycol | 2.50 | — |
| | Hexylene Glycol | — | 2 |
| B | Oxybenzone | 4.00 | — |
| | Octyl Methoxycinnamate | 7.50 | 7.5 |
| | Octyl Salicylate | 4.00 | 3 |
| | Benzophenone-3 | — | 3 |
| | Octyl Palmitate | — | 6 |
| | PEG-20 Stearate | — | 2 |
| | Glyceryl Stearate & Laureth-23 | — | 5 |
| | Polydecene | 7.50 | — |
| | Ethylhexylpalmitate | 5.00 | — |
| | Octocrylene | 10.00 | — |
| | Cetearyl Alcohol (And) Ceteareth-20 | 1.00 | — |
| C | Polymers 1-9 or Comparative Example A | 2 | 1 |
| D | Triethanolamine 99% | 0.35 | 0.2 |
| E | Preservative | 1.00 | 1.1 |

The sunscreen formulations are prepared by adding all phase A ingredients into a container and heating to 75° C. All phase B ingredients are added to another container and heated to 75° C. to ensure oxybenzone well dissolved. Then phases A and B are combined with high sheer. The solution is cooled to 55-60° C. and phase D ingredients are added. When temperature reaches 45° C., phase C ingredients are added. Add phase E when the temperature is below 40° C. Adjust pH to 6.0-7.0.

All samples are tested using. In Vitro SPF/UVA measurements made both prior to, and after the samples have been immersed in a controlled temperature water bath: 40° C.—agitated at 300 rpm—for 80 minutes by using VITRO-SKIN® Substrate. The water resistance test result is ranked with the following scale based on SPF retention:

Poor: 0-15% SPF retention
Fairly Good: 16-40% SPF retention
Good: 41-64% SPF retention
Excellent: above 65% SPF retention For the aesthetic evaluation, 5 panelists participate in each panel test. Panelists' forearms are marked 3 cm×4 cm sites with Skin-Marker. Panelists spread the product evenly with index and middle fingers in circular motion until the sample is evenly distributed. The Tackiness Score ranges between most tacky (5) and least tacky (1). Each of example samples were then evaluated by panelists and their scores were recorded and averaged and reported in TABLE 5.

TABLE 5

| Polymer | Formulation Aesthetic Results | Formulation SPF Retention (%)* |
| --- | --- | --- |
| Comparative example A | 5 | Good |
| Comparative example B (no polymer) | 1 | Poor |
| Polymer 1 | 3.3 | Excellent |
| Polymer 2 | 2.4 | Excellent |
| Polymer 3 | 2.6 | Excellent |
| Polymer 4 | 2.7 | Excellent |
| Polymer 5 | 2.1 | Good |
| Polymer 6 | 4.7 | Excellent |
| Polymer 7 | 3.7 | Excellent |
| Polymer 8 | 2.6 | Excellent |
| Polymer 9 | 1.8 | Excellent |

Accordingly, all of the inventive samples outperformed the relevant comparative sample.

The invention claimed is:

1. A personal care composition comprising a polymer comprising:
    (a) one or more polymer comprising, as polymerized units,
        (i) 14% to 20% by weight of butyl acrylate monomer, 38.5% to 47.575% by weight of methyl methacrylate monomer, and 1.35% to 1.5% by weight of methacrylic acid monomer, all being based on the weight of the polymer, and
        (ii) 28 to 40% by weight, based on the weight of the polymer, of ethylhexyl acrylate monomer,
        (iii) 0.01% to 0.3% by weight, based on the total weight of the polymer, of allyl methacrylate, and,
    (b) at least one suncare active.
2. The personal care composition of claim 1, wherein the suncare active is at least one of octyl methoxycinnamate, avobenzone, para aminobenzoic acid, homosalate, titanium dioxide, zinc oxide, benzophenones, benzylidenes, octyl crylene, or salicylates.
3. The personal care composition of claim 1, wherein the polymer is formed in a single stage.
4. The personal care composition of claim 1, wherein the polymer is formed in a two stage reaction.
5. The personal care composition of claim 4, wherein the stage 1 and stage 2 ratio ranges from 60:40 to 99 to 1.
6. The personal care composition of claim 4, wherein the polymer is a polymer comprising stage 1 in an amount of 85 weight % and stage 2 in an amount of 15 weight %, based on the total weight of the polymer, wherein stage 1 comprises, as polymerized units, based on the weight of stage 1, 20 parts by weight butyl acrylate/40 parts by weight ethylhexyl acrylate/38.5 parts by weight methyl methacrylate/1.5 parts by weight methacrylic acid/0.075 parts by weight allyl methacrylate, and wherein stage 2 comprises, as polymerized units, based on the weight of stage 2, 99 parts by weight methyl methacrylate and 1 methacrylic acid.

* * * * *